United States Patent [19]

Katsoulis

[11] Patent Number: 5,017,360

[45] Date of Patent: May 21, 1991

[54] SURFACE MODIFIED ALUMINUM AND ALUMINUM-ZIRCONIUM SALTS

[75] Inventor: Dimitris E. Katsoulis, Midland, Mich.

[73] Assignee: Dow Corning Corporation, Midland, Mich.

[21] Appl. No.: 511,686

[22] Filed: Apr. 20, 1990

[51] Int. Cl.$^5$ .................. A61K 7/32; A61K 7/34; A61K 7/38

[52] U.S. Cl. ........................ 424/45; 424/47; 424/682

[58] Field of Search .............. 424/45, 66, 47

[56] References Cited

U.S. PATENT DOCUMENTS

| | | | |
|---|---|---|---|
| 4,152,416 | 5/1979 | Spitzer | 424/65 |
| 4,174,386 | 10/1979 | Spitzer | 424/65 |
| 4,690,817 | 9/1987 | Davis | 424/66 |
| 4,822,603 | 5/1989 | Farris | 424/66 |
| 4,863,721 | 9/1989 | Beck | 424/66 |
| 4,919,934 | 5/1990 | Deckner | 424/66 |
| 4,944,937 | 7/1990 | McCall | 424/68 |
| 4,948,578 | 8/1990 | Burger | 424/68 |

FOREIGN PATENT DOCUMENTS

| | | |
|---|---|---|
| 2275088 | 4/1989 | Australia . |
| 0326155 | 8/1989 | European Pat. Off. . |
| 1536222 | 12/1978 | United Kingdom . |

Primary Examiner—Thurman Page
Assistant Examiner—Demetra Mills
Attorney, Agent, or Firm—Sharon K. Severance

[57] ABSTRACT

Novel aluminum and aluminum-zirconium salts are produced by reacting aluminum or aluminum-zirconium halohydrate with an anionic lipophilic component. These salts are useful in antiperspirant compositions or as rheological additives. Also disclosed is a novel process of producing oil-in-water emulsions whereby the novel aluminum or aluminum-zirconium salt functions as a surfactant upon forming.

12 Claims, No Drawings

SURFACE MODIFIED ALUMINUM AND ALUMINUM-ZIRCONIUM SALTS

Novel aluminum and aluminum-zirconium salts are formed by modifying aluminum halohydrate and aluminum-zirconium-halohyrates by the attachment of an anionic lipophilic compound. The novel aluminum and aluminum-zirconium salts have hydrophobic characteristics and are useful in antiperspirant compositions.

BACKGROUND OF THE INVENTION

Antiperspirant salts are composed of cationic metal oxide part of aluminum and aluminum-zirconium and an anionic part of a halide such as $Cl^-$ and less commonly $Br^-$ or $I^-$. Nitrate salts are also known in the art. These antiperspirant salts, due to their cationic/anionic characteristics, are soluble in water.

Typical aluminum halohydrate salts are believed to be composed of five cationic components. Evidence also exists that aluminum-zirconium-glycine salts are composed of two zirconium species, heteronuclear aluminum-zirconium oligomeric components as well as the five aluminum halohydrate species. In either the aluminum or the aluminum-zirconium salts, a high degree of hydrogen-bonding exists, especially at high solid concentrations. The halohydrate salts, when in highly concentrated solutions, are large agglomerates of charged polyoxides, and their positive charge is counter balanced by the negatively charged halide or nitrate ions.

In recent years a lot of interest has been expressed in decreasing the hydrophilic character of the salts, and creating materials that are more compatible with the hydrophobic nature of their delivery system. One way of introducing hydrophobic properties into the salts, which is encompassed by this invention, is to modify the cationic surface of the salt by attaching an anionic lipophilic component chain to the salt. Carboxylate, sulfate and phosphate compounds are useful as the anionic lipophilic component.

The use of carboxylic acids in antiperspirant formulations is known in the art. For example U.S. Pat. No. 4,174,386 to Spitzer et al. teaches a highly concentrated aerosol antiperspirant composition which contains 0 1 to 5 weight percent of a solid saturated aliphatic carboxylic acid having 14 to 22 carbon atoms in a straight chain. The solid saturated aliphatic carboxylic acid is blended into the formulation and is not used to directly alter the antiperspirant salt nor is it taught to react with the antiperspirant salt in any manner. The use of the solid saturated aliphatic carboxylic acid improves the adherence of the antiperspirant salt to the skin.

Modification of antiperspirant or aluminum salts using organic materials to obtain certain properties is also known in the art. GB Patent No. 1536222 to Shelton teaches an anhydrous antiperspirant composition which contains 10 to 30 weight percent of an alcohol-soluble antiperspirant salt complex. The alcohol-soluble antiperspirant salt complex is produced by reacting an astringent antiperspirant salt with a polyhydric alcohol. These salt complexes may be formulated into mechanically sprayable (not aerosol) antiperspirant compositions. Additionally, EP Patent No. 326155 to Fukasawa teaches a novel polyaluminum dialkylphosphate that is useful as an oil gelling agent. The polyaluminum dialkylphosphates are produced by reacting a dialkyl phosphate with a polyaluminum salt. The compositions taught by Fukasawa are not shown to have any use in antiperspirants or to have any antiperspirant activity.

Further, Australian Patent No. 22750 to Schang et al. teaches novel aluminum-magnesium salts that are produced through the reaction between an aluminum-magnesium-hydroxy sulfate clay and a salt of a carboxylic acids, such as sodium caprylate. The aluminum-magnesium clays are insoluble in water and the reaction is carried out as a suspension of the two solid reagents in water. Aluminum and aluminum-zirconium halohydrate salts which are used in the instant invention are very different in structure and chemistry from the Al/Mg synthetic clays used in the Australian 22750 patent.

It is an object of this invention to show novel aluminum and aluminum-zirconium salts that contain anionic lipophilic groups.

It is further an object of this invention to show a method for producing the novel aluminum and aluminum-zirconium salts.

It is further an object of this invention to show the use of the novel aluminum and aluminum-zirconium salts in antiperspirant compositions.

It is further an object of this invention to show the use of the novel aluminum and aluminum-zirconium salts as suspending agents.

It is further an object of this invention to show the use of the novel aluminum and aluminum-zirconium salts as rheological additives.

It is further an object of this invention to show a method for producing emulsions which in which the novel aluminum and aluminum-zirconium salts function as the surfactants.

THE INVENTION

Novel aluminum and aluminum-zirconium salts are produced from the reaction between an aluminum halo- or nitro- hydrate (herein referred to only as halohydrate) or aluminum- zirconium halo- or nitro- hydrate (herein referred to as only halohydrate) with an anionic lipophilic (herein referred to as organophilic) compound. These novel aluminum and aluminum-zirconium salts have a higher degree of hydrophobicity than their non organophilic containing counterparts.

The organophilic compounds useful in the instant invention are selected from monovalent alkyl carboxylates, polyvalent alkyl carboxylates, acyl lactylates, alkyl ether carboxylates, N-acyl sarcosinates, N-acyl glutamates, fatty acid-peptide condensates, alkyl sulfates, ethoxylated alkyl sulfates, alpha olefin sulfonates, and phosphated ethoxylated alcohols and others. Preferred organophilic compound are those which are acceptable in cosmetic applications.

The monovalent alkyl carboxylates useful in the instant invention can be exemplified by the formula

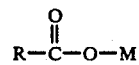

wherein R is selected from a saturated or unsaturated branched or linear alkyl group consisting of at least 1 carbon atom; and M is selected from the hydrogen atom, an alkali metal and ammonium.

R may be further exemplified by methyl, ethyl, propyl, octyl, decyl, undecyl, pentadecyl, hexadecyl, octadecyl, and doeicosyl. M may be further exemplified by the hydrogen atom, ammonium, lithium, potassium and sodium.

Monovalent carboxylates useful in the instant invention may be further exemplified by, but are not limited to, butyric acid, caprylic acid, lauric acid, palmitic acid, stearic acid, behenic acid, oleic acid, linoleic acid, linolenic acid, ammonium caprylate, ammonium palmitate, sodium stearate, potassium stearate and others.

The polyvalent alkyl carboxylates useful in the instant invention can be exemplified by the formula

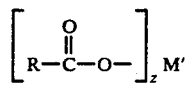

wherein each R is independently selected from a saturated or unsaturated branched or linear alkyl group consisting of at least 1 carbon atom; M' is selected from an alkaline earth metal, aluminum and zinc; and z has a value of 2 and 3. M' may be further exemplified by, aluminum, zinc, magnesium, barium and calcium.

Polyvalent carboxylates useful in the instant invention may be further exemplified by barium propionate, magnesium butyrate, zinc valerate, zinc caprylate, aluminum palmitate, calcium stearate, magnesium stearate, aluminum stearate and others.

The acyl lactylates useful in the instant invention can be exemplified by the formula

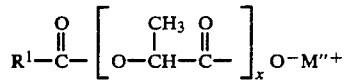

wherein $R^1$ is selected from a saturated or unsaturated branched or linear alkyl group consisting of 8 to 25 carbon atoms; M" is selected from an alkali and alkaline earth metal and x has the value of 1 and 2.

$R^1$ may be further exemplified by caprylic, stearic, behenic and others. M" may be further exemplified by, sodium, potassium, calcium, barium and magnesium.

The acyl lacylates useful in the instant invention may be produced from the esterification of one mole of a fatty acid with at least two moles of lactic acid. For example, the acyl lacylates may be produced from the esterification reaction between lauric acid and lactic acid or between stearic acid and lactic acid. Additional fatty acids that may used to produce the acyl lacylates include, but are not limited to, behenic, pelargonic, capric, palmitic, margaric, arachidic and others.

The alkyl ether carboxylates useful in the instant invention can be exemplified by the formula

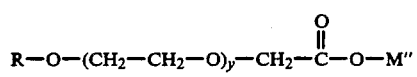

wherein R is selected from a saturated or unsaturated branched or linear alkyl group consisting of at least 1 carbon atoms; M" is selected from an alkali and alkaline earth metal and y has the value of 1 to 10.

The alkyl ether carboxylates may be further exemplified by sodium trideceth-12 carboxylate, sodium laureth-2 carboxylate, $C_{13}H_{27}O(CH_2CH_2O)_{11}CH_2COONa$ and others.

The N-acyl sarcosinates useful in the instant invention can be exemplified by the formula

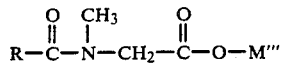

wherein R is selected from a saturated or unsaturated branched or linear alkyl group consisting of at least 1 carbon atom; and M''' is selected from alkali metals.

The N-acyl sarcosinates useful in the instant invention may be further exemplified by sodium N-lauroyl sarcosinate, cocoyl sarcosinate, tetraethanolamine sarcosinate, stearoyl sarcosinate and others.

The N-acyl glutamates useful in the instant invention can be exemplified by the formula

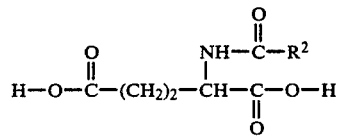

wherein $R^2$ is selected from a saturated or unsaturated branched or linear alkyl group consisting of 10 to 20 carbon atoms $R^2$ may be further exemplified by lauryl, stearyl, hexadecanyl, heptadecanyl, eisconanyl and others.

The N-acyl glutamates useful in the instant invention may be further exemplified by TEA-cocyl glutamate, sodium lauroyl glutamate, and others.

The fatty acid-polypeptide condensates useful in the instant invention can be exemplified by

wherein R is selected from a saturated or unsaturated branched or linear alkyl group consisting of at least 1 carbon atom.

The fatty acid-polypeptide condensates useful in the instant invention are typically produced through the condensation reaction between a fatty acid and the amino group of a protein hydrolyzate. The acids useful in producing the fatty acid-polypeptide condensates include, but are not limited to, lauric, palmitic, cocoic, oleic, stearic, undecyleric and others.

The alkyl sulfates useful in the instant invention can be exemplified by

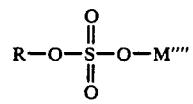

wherein R is selected from a saturated or unsaturated branched or linear alkyl group consisting of at least 1 carbon atom; and M'''' is selected from the hydrogen atom, an alkali metal, an alkaline earth metal and ammonium.

The alkyl sulfates useful in the instant invention may be further exemplified by methylsulfuric acid, sodium methyl sulfate, ethylsulfuric acid, potassium ethyl sulfate, sodium lauryl sulfate, sodium dodecyl sulfate and others.

The ethoxylated alkyl sulfates useful in the instant invention can be exemplified by

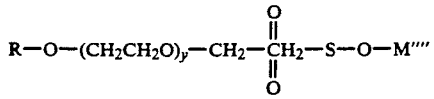

wherein R is selected from a saturated or unsaturated branched or linear alkyl group consisting of at least 1 carbon atom; M'''' is selected from the hydrogen atom, an alkali metal, an alkaline earth metal and ammonium; and y has the value of 1 to 10.

Ethoxylated alkyl sulfates useful in the instant invention may be further exemplified by sodium nonoxynol-n sulfate, sodium trideceth-n sulfate and others.

The alpha olefin sulfonates useful in the instant invention can be exemplified by

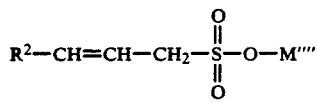

wherein $R^2$ is selected from a saturated or unsaturated branched or linear alkyl group consisting of 10 to 20 carbon atoms; and M'''' is selected from the hydrogen atom, an alkali metal, an alkaline earth metal and ammonium.

The alpha olefin sulfonates useful in the instant invention may be produced by continuous sulfonation with $SO_3$ of an olefin derived from the oligomerization of ethylene or from thermal cracking of the appropriate hydrocarbons. This procedure results in a fairly complex mixture of products. Most commonly known alpha olefin sulfonates are sodium $C_{14}$ to $C_{16}$ olefin sulfonates.

The phosphated ethoxylated alcohols useful in the instant invention may be further exemplified by

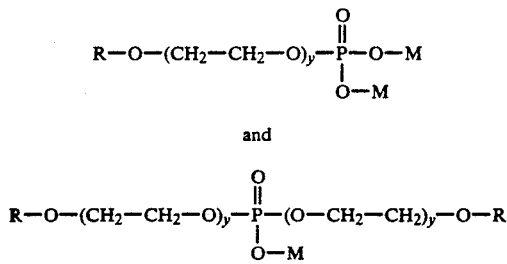

wherein R is selected from a saturated or unsaturated branched or linear alkyl group consisting of at least 1 carbon atom; M is selected from the hydrogen atom, an alkali metal and ammonium; and y has the value of 1 to 10.

The phosphated ethoxylated alcohols useful in the instant invention may be further exemplified by, but are not limited to, polyethylene (3) oleyl ether phosphate, polyethylene (10) oleyl ether phosphate, polyethylene (10) polyoxypropylene (5) ether phosphate and others.

Other organophilic compounds which may be similar in structure and properties to the organophilic compounds listed above may also be useful in the instant invention.

The organophilic compounds are reacted with halohydrate salts of aluminum or aluminum-zirconium or mixtures thereof to produce the novel aluminum and aluminum-zirconium salts. The aluminum halohydrate and aluminum-zirconium halohydrate salts may be exemplified by aluminum chlorohydrate, aluminum iodohydrate, aluminum bromohydrate, aluminum nitrohydrate, aluminum-zirconium chlorohydrate, aluminum-zirconium iodohydrate, aluminum-zirconium bromohydrate, aluminum-zirconium nitrohydrate and others. The aluminum-zirconium halohydrate salts useful in the instant invention also encompass the amino acid complexes of the above mentioned aluminum-zirconium halohydrate salts. The aluminum halohydrate and aluminum-zirconium halohydrate salts useful in the instant invention are commercially available or may be produced using methods known in the art.

Aluminum chlorohydrate and aluminum-zirconium chlorohydrate are the preferred aluminum halohydrate and aluminum zirconium halohydrate salts useful in the instant invention due to their commercial availability. The aluminum chlorohydrate salts useful in the instant invention are commonly represented, for example, by the formula $Al_2(OH)_5Cl \cdot mH_2O$ where m has the value of 1 or greater. The aluminum-zirconium-glycine chlorohydrate salts useful in the instant invention are commonly represented, for example, by the formula $Al_4Zr(OH)_{12}Cl_4 \cdot (H_2NCH_2COOH) \cdot mH_2O$ where m is as described above.

The aluminum and aluminum-zirconium halohydrate salts are most often composed of a mixture of various polymeric species. It is feasible to isolate a single polymeric species from the mixture or to produce a single polymeric species using methods known in the art. The single polymeric species can be reacted with the organophilic compound in the same manner as the mixtures to form a novel aluminum or aluminum-zirconium salt. However, the aluminum and aluminum-zirconium salt mixtures are the preferred reactants due to their commercial availability and ease of manufacture.

The novel aluminum salt compositions may be represented, for example by a composition having an empirical formula $Al_a(OH)_b(Z)_cCl_d$ wherein Z is an anionic part of an organophilic compound; $a/(c+d)$ has the value of 0 to 3, inclusive; $c+d=3a-b$; and c is greater than 0. The novel aluminum zirconium salt compositions may be represented, for example, by a composition having an empirical formula $Al_kZr_m(OH)_n(Z)_pCl_q$ wherein Z is as described previously; $k/m$ is greater than 0; $3k+4m=n+p+q$; and p is greater than 0. For use as antiperspirant actives it is preferred that $k/m$ have the value of 2 to 10. inclusive. The formulas for the novel aluminum and aluminum-zirconium salts are a simplification of the various components and are not to be interpreted as the presence of only one component. The aluminum-zirconium salts may further contain an amino acid in amounts approximately equivalent to the amount of zirconium on a molar basis.

Two reaction mechanisms can be used to produce the novel aluminum and aluminum-zirconium salts. When the salt of the organophilic compound is used as the reactant, the novel aluminum and aluminum-zirconium salts are produced using a metathesis reaction. When the acid form of the organophilic compound is used as the reactant, the novel aluminum and aluminum-zirconium salts are produced through a phase transfer type of reaction.

A metathesis reaction is a reaction involving the exchange of elements or groups. For example, the reaction between aluminum chlorohydrate and sodium stearate results in the formation of aluminum polyoxo-stearate and sodium chloride. The reaction can be carried out using less than the stoichiometric amount of organophilic compound necessary to exchange with the halide or nitrate ions. Thus, in the reaction between aluminum chlorohydrate and sodium stearate, the result can be a novel aluminum salt comprising a mixture of aluminum polyoxo-chlorostearate.

The metathesis reaction is carried out by combining the aluminum or aluminum-zirconium halohydrate and the organophilic compound in an aqueous, aqueous/alcohol or aqueous/solvent medium and precipitating out the novel aluminum or aluminum-zirconium salt. The preferred medium, in which the reaction takes place, should be one in which the reaction components are both soluble. When the reaction medium is comprised of protic solvents, such as water and alcohols, the reaction is usually spontaneous. Additionally, the novel aluminum and aluminum-zirconium salts are insoluble in the protic solvent and almost instantly precipitate out. When the novel aluminum or aluminum-zirconium salts do not fully or readily precipitate out of the solution, they may be recovered by evaporation of the medium. However, due to the physical nature of the novel salts, this is rarely necessary.

The conditions for the metathesis reaction are typically at room temperature and atmospheric pressure. However, pressures above or below atmospheric may also be suitable. Temperatures above room temperature may also be suitable when one of the reactants needs the aid of heat to dissolve in the reaction medium. It is preferred that the temperature of the reaction medium be maintained below the boiling point of that medium and more preferably below 100° C.

The amount of organophilic component reacted with the aluminum or aluminum halohydrate salt is dependent on the amount of halogen ion contained in the salt. A simple titration reaction can be done with the halohydrate salt and organophilic compound to determine the amount of organophilic component necessary to result in a complete or essentially complete reaction. This titration reaction comprises adding an incremental amount of sodium stearate to an aqueous solution of the aluminum or aluminum-zirconium halohydrate salt, allowing any formed novel salt to precipitate and settle out of the solution and using HPLC techniques known in the art to measure the amount of unreacted aluminum or aluminum-zirconium halohydrate salt which remains in the solution. Preferably, an excess of the organophilic compound should be used for a complete or a nearly complete reaction whereby essentially all of the halide or nitrate ions are exchanged for the anionic portion of the organophilic group.

The other reaction which is useful for producing the novel aluminum and aluminum-zirconium salts is a phase transfer reaction. The phase transfer reaction comprises creating two solutions each comprising soluble ions of one of the reactive components. The two solutions are mixed or emulsified together resulting in ions being transferred across the phases and the formation of the novel aluminum or aluminum-zirconium salts contained in an emulsion or mixture of the two medium.

The solutions are created by dissolving each reactive component in a medium in which it is soluble. Medium useful for solubilizing the aluminum or aluminum-zirconium halohydrate salt include water, water/solvent systems and water/alcohol systems. Water is the preferred medium for solubilizing the halohydrate salts. The aluminum or aluminum-zirconium salt solutions typically contain 1 to 50 weight percent of the aluminum or aluminum-zirconium salt.

Medium useful for solubilizing the organophilic compound include cyclic or linear siloxanes such as dimethicone or cyclomethicone and hydrocarbons such as n-octane and isoparaffin. Cyclic or linear siloxanes are the preferred medium for the organophilic compound. The amount of organophilic compound which can be contained in the medium is dependent upon the solubility properties of the organophilic compound in the chosen medium.

It may be necessary to apply heat to one or both of the medium to aid in the solubilization of the reactive component. Typically temperatures below the boiling points of the medium are suitable for achieving solubilization of the component. The two medium are then combined by mixing, agitating, shaking or using other mechanical means such as homogenizers.

Upon the combination of the two medium containing the reaction components, a reaction occurs which results in the formation of the novel aluminum or aluminum-zirconium salt. This reaction is unique in that the novel salt formed has the characteristics of a surfactant and thereby when the medium are combined in the manner described above, an oil in water type emulsion may he formed.

The method for forming the oil-in-water emulsions comprises combining an aqueous solution which contains the aluminum or aluminum-zirconium halohydrate salt with an "oil" solution containing the organophilic compound. As the two solutions are combined together with some means of agitation such as stirring, shaking, homogenizing and others, a reaction takes place forming the novel aluminum or aluminum zirconium salt. This salt functions as a surfactant which in turn aids in the formation of an emulsion. The emulsions produced by this method are typically of the oil-in-water type and are standard or macro emulsions.

During the process of combining the medium, or during the course of the reaction, heat may be optionally applied. Heat is typically applied when needed to maintain solubilization of a component in its medium or as an aid when combining two medium. When using heat prior to or during the course of the reaction it is preferred that the temperature be maintained below the boiling point of the medium and more preferably below 100° C. The reaction is typically run at atmospheric pressure. However, pressures above or below atmospheric may also be suitable.

The novel aluminum or aluminum-zirconium salt may be recovered from the emulsion using evaporation techniques known in the art to remove the reaction medium and precipitate out the salt. When applying heat to the emulsion to aid in the evaporation of the medium it is preferred to use temperatures below the boiling point of the medium and more preferably below 100° C.

The amount of organophilic compound which is reacted with the aluminum or aluminum-zirconium halohydrate salt is dependent on the halogen ion concentration in the salt and the ability for the components used to result in the formation of an emulsion. The formation of an emulsion is a function of the aluminum or aluminum-zirconium halohydrate salt, the organophilic compound, their respective medium and the concentrations of each. The quantities of the reactants and their respective medium which will result in the formation of an emulsion can be readily determined by one skilled in the art.

The novel aluminum and aluminum-zirconium salts of the instant inVention are useful as antiperspirant actives in the formulation of aerosol, roll-on and stick type antiperspirant compositions in which the salts are dissolved in organic media, oils and silicones. The antiperspirant compositions are produced using known formulations wherein the aluminum chlorohydrate or aluminum-zirconium-glycine chlorohydrate salt is replaced with the novel aluminum or aluminum-zirconium salts.

A typical aerosol antiperspirant composition is comprised of the novel aluminum salt, a suspension aid, a carrier liquid such as a volatile silicone and a propellant. Optional ingredients which can be added into the aerosol antiperspirant composition include alcohols, fragrances, talc, preservatives, antimicrobials, lubricants, gel inhibitors, other carrier liquids such as carboxylic esters, and other materials Which may improve the aesthetics. Concentrations of the components in the aerosol composition may vary depending on the formulation, however, the novel aluminum salt is limited by Food and Drug Administration regulations to about 25 percent by weight of the total composition.

A typical roll-on antiperspirant composition comprises the novel aluminum or aluminum-zirconium salt, and a delivery means selected from a volatile silicone, alcohols, water, other solvents, and mixtures thereof. Optional ingredients which can be added into the roll-on antiperspirant composition include surfactants, preservatives, antimicrobials, fillers, fragrances, emollients, suspension aids and other materials which may improve the aesthetics. Concentrations of the components in the roll-on composition may vary depending on the formulation, however, the novel aluminum salt is limited to about 25 percent by weight and the novel aluminum-zirconium salt is limited to about 20 percent by weight of the total composition by Food and Drug Administration regulations.

A typical stick antiperspirant composition comprises the novel aluminum or aluminum-zirconium salt, a solidifier such a stearyl alcohol and cetyl alcohol, and a volatile silicone or other hydrophobic liquid. Optional ingredients which can be added into the stick antiperspirant composition include surfactants, fragrances, preservatives, fillers, antimicrobials and other materials which may improve the aesthetics. Concentrations of the components in the stick composition may vary depending on the formulation, however, the novel aluminum salt is limited to about 25 percent by weight and the novel aluminum-zirconium salt is limited to about 20 percent by weight of the total composition by Food and Drug Administration regulations.

The emulsions formed using the phase transfer type reaction containing the novel aluminum or aluminum zirconium salts may be used directly as antiperspirant compositions. Additional ingredients which may improve the aesthetics of the solution but will not affect the stability of the emulsion may be added. These include preservatives, emollients, antimicrobials, lubricants, fragrances, fillers, and others.

Further, the novel aluminum or aluminum-zirconium salts are useful in improving the suspension characteristics of antiperspirant actives. The antiperspirant actives of which suspension is improved are those known in the art. They may be exemplified by aluminum chlorohydrate, aluminum iodohydrate, aluminum bromohydrate, aluminum nitrohydrate, aluminum-zirconium chlorohydrate, aluminum-zirconium iodohydrate, aluminum-zirconium bromohydrate, aluminum-zirconium nitrohydrate and others. The aluminum-zirconium halohydrate salts also encompass the amino acid complexes of the above mentioned aluminum-zirconium halohydrate salts. The novel aluminum or aluminum-zirconium salts may be added as suspension aids at levels of 1 to 15 percent by weight.

Further, the novel aluminum or aluminum-zirconium salts are useful as rhelogical additives. When the novel aluminum or aluminum-zirconium salts are added into a hydrophobic liquid (such as silicones, mineral oil, hydrocarbons, alkanes, isoparaffins, and others) at levels of 0.5 to 30% by weight, changes in the rheological properties of the hydrophobic liquid will occur. These changes can include either a decrease or an increase in the viscosity of the fluid when measured under shear. Polar activators can be additionally added (typically at levels of 0.5 to 15 percent by weight of the novel aluminum or aluminum-zirconium salt) to further enhance the novel salts ability to change the rheological properties. Polar activators can be selected from polar solvents and alcohols.

Additionally the novel aluminum or aluminum-zirconium salts may be useful as hardening agents, pigments, gellants, and homogeneous and/or heterogeneous catalysts.

So that those skilled in the art can understand and appreciate the invention taught herein, the following examples are presented, it being understood that these examples should not be used to limit the scope of this invention over the limitations found in the claims attached hereto.

EXAMPLE 1

40 grams of sodium stearate was dissolved in 760 grams of deionized water at 90° C. In a separate beaker, 100 grams of aluminum chlorohydrate powder was dissolved in 400 grams deionized water. The aluminum chlorohydrate solution was added slowly to the sodium stearate solution while allowing the temperature to cool to 60° C. and while being stirred. The precipitate was filter using #1 filter paper and allowed to dry in a vacuum dessicator for several days. The resulting powder was extremely fine and light. The novel aluminum salt was analyzed using elemental analysis. Result show 2.94% Cl, 45.43% C, 9.02% H, and 11.9% Al. The starting aluminum chlorohydrate had an elemental analysis of 8.15% Cl and 12.45% Al.

EXAMPLE 2

10 grams of aluminum chlorohydrate was dissolved in 100 ml of water. 26.8 grams of stearic acid was dissolved in 100 ml of cyclic siloxanes at approximately 70° C. The aqueous aluminum chlorohydrate solution was added to the stearic acid solution with stirring. The solution was heated to 80° C. A thin homogeneous white creme paste resulted. At room temperature it was viscous and waxy. The sample was allowed to dry by evaporation over a period of several days. A dry white powder resulted.

EXAMPLE 3

40 grams of sodium stearate was dissolved in 760 grams of deionized water at 90° C. In a separate beaker, 50 grams of aluminum-zirconium-glycine chlorohydrate powder was dissolved in 450 grams deionized water. The sodium stearate solution was added slowly to the aluminum-zirconium-glycine chlorohydrate solution while being stirred. The solution thickened considerably. The precipitate was filter using gravity while hot. The resulting powder was extremely fine and light.

EXAMPLE 4

2.5 grams of stearic acid was stirred into 35.0 grams of cyclic siloxanes and heated until the stearic acid had melted. To that solution, a 50 gram solution of 50% by weight aluminum-zirconium-glycine chlorohydrate in water was added while stirring. The mixture was transferred to a separatory funnel and shaken vigorously for 4 to 5 minutes. An emulsion was formed with a very thin (less than ⅛ inch) layer of clear liquid on top. The emulsion showed no further separation after 3 months.

EXAMPLE 5

A sodium caprylate solution was prepared by dissolving 40 grams of sodium caprylate into 760 grams of deionized water at 26° C. An aluminum chlorohydrate solution was prepared as in Example 1. Both solutions were heated to 30° C. The sodium caprylate solution was slowly added to the aluminum chlorohydrate solution with stirring. The precipitate was filtered under vacuum using #1 filter paper and dried in a vacuum dessicator. The solid was analyzed by elemental analysis and was shown to contain 1.60% Cl, 20.68% C, 6.41% H and 10.5% Al. The starting aluminum chlorohydrate was the same as used in Example 1.

EXAMPLE 6

4 grams of dodecyl sodium sulfate was dissolved in 76 grams if deionized water using heat. In a separate beaker, 10 grams of aluminum chlorohydrate powder was dissolved in 40 grams deionized water. The aluminum chlorohydrate solution and the dodecyl sodium sulfate solution were combined with mixing. The precipitate was filtered. The resulting precipitate had a thick, white, creamy appearance.

EXAMPLE 7

2.5 grams of behenic acid was stirred into 35.0 grams of cyclic siloxanes and heated until the behenic acid had melted. To that solution, a 50 gram solution of 10% by weight aluminum chlorohydrate in water was added while stirring. The mixture was transferred to a separatory funnel and shaken vigorously for 4 to 5 minutes. An emulsion was formed. There was a small layer of oil on top.

EXAMPLE 8

2.50 grams of caprylic acid was stirred into 35.0 grams of cyclic siloxanes and heated until the caprylic acid had melted. To that solution, a 50 gram solution of 10% by weight aluminum chlorohydrate in water was added while stirring. The mixture was transferred to a separatory funnel and shaken vigorously for 4 to 5 minutes. An emulsion was formed. After settling the emulsion had about 25 grams of clear liquid on top and a thicker white liquid on the bottom.

EXAMPLE 9

2.51 grams of stearic acid was stirred into 47.49 rams of cyclic siloxanes and heated until the stearic acid had melted. To that solution, a 50 gram solution of 50% by weight aluminum chlorohydrate in water was added while stirring. The mixture was transferred to a separatory funnel and shaken vigorously for 4 to 5 minutes. An oil free emulsion was formed.

EXAMPLE 10

1.50 grams of stearic acid was stirred into 36.0 grams of cyclic siloxanes and heated until the stearic acid had melted. To that solution, a 51 gram solution of 50% by weight aluminum chlorohydrate in water was added while stirring. The mixture was transferred to a separatory funnel and shaken vigorously for 4 to 5 minutes. An oil free emulsion was formed.

EXAMPLE 11

2.5 grams of stearic acid was stirred into 35.0 grams of cyclic siloxanes and heated until the stearic acid had melted. To that solution, a 50 gram solution of 10% by weight aluminum chlorohydrate in water was added while stirring. The mixture was transferred to a separatory funnel and shaken vigorously for 4 to 5 minutes. An oil free emulsion was formed.

EXAMPLE 12

2.5 grams of stearic acid was stirred into 35.0 grams of 5 centistoke DOW CORNING 200 FLUID and heated until the stearic acid had melted. To that solution, a 50 gram solution of 10% by weight aluminum chlorohydrate in water which had been heated to 60° C. was added while stirring. The mixture was transferred to a separatory funnel and shaken vigorously for 4 to 5 minutes. An emulsion was formed. There was no liquid separation.

A second emulsion was formed using the same quantity of ingredients, except 100 centistoke DOW CORNING 200 FLUID was used in place of the 5 centistoke fluid. The emulsion was a very thick paste and there was no liquid separation.

EXAMPLE 13

2.5 grams of stearic acid was stirred into 35.0 grams of n-octane and heated until the stearic acid had melted. To that solution, a 50 gram solution of 10% by weight aluminum chlorohydrate in water which had been heated to 60° C. was added while stirring. The mixture was transferred to a separatory funnel and shaken vigorously for 4 to 5 minutes. An emulsion was formed. There was a very small amount (<2%) of clear liquid on the top.

EXAMPLE 14

2.5 grams of stearic acid was stirred into 35.0 grams of paraffin oil and heated until the stearic acid had melted. To that solution, a 50 gram solution of 10% by weight aluminum chlorohydrate in water which had been heated to 60° C. was added while stirring. The mixture was transferred to a separatory funnel and shaken vigorously for 4 to 5 minutes. An thick, white emulsion was formed. A small amount of clear liquid was on the bottom.

EXAMPLE 15

An antiperspirant composition was produced by mixing 10 grams of aluminum-polyoxo chlorostearate, produced using the phase transfer type reaction (aluminum chlorohydrate and stearic acid), with 25 grams deionized water, 20 grams of cyclomethicone, and 2.0 grams of Elfacos St-37 (PEG22 dodecyl glycol co-polymer manufactured by AKZO CHEMIE). The antiperspirant composition was a creamy fluid. When applied to the skin it has a smooth feel and is not tacky. The antiperspirant composition did not show any signs of separation.

A second antiperspirant composition was produced using aluminum chlorohydrate. The antiperspirant composition was a thin emulsion that separated rather quickly. When applied to the skin it has a smooth feel and is not tacky.

EXAMPLE 16

An antiperspirant roll-on composition was produced using 70 grams of cyclomethicone, 2 grams of DOW CORNING 3225C, 5 grams of aluminum chlorohydrate and 3 grams of aluminum polyoxo chlorostearate produced in Example 1. The components were thoroughly mixed. After settling overnight, it was moderately easy to re-disperse the aluminum chlorohydrate using shaking.

A comparative roll-on was produced using 70 grams of cyclomethicone, 2 grams of DOW CORNING 3225C, and 5 grams of aluminum chlorohydrate. After settling overnight, it was difficult to re-disperse the aluminum chlorohydrate using shaking.

EXAMPLE 17

The rheological properties of trimethylendblocked polydimethylsiloxane (350 centistoke) was studied using varying amounts of the aluminum polyoxo chlorostearate produced in Example 1 and the aluminum polyoxo chlorocaprylate produced in example 5 as rheological additives. Small amounts of Ethanol 200 was added as a polar activator. Table 1 shows the amount of additive, ethanol and the viscosity of the fluid measured using a Brookfield DV II Cone and Plate Viscometer with a #52 spindle at 28° C. Sample A is the fluid without any additive. Samples B, C and D contain the aluminum polyoxo chlorostearate and Samples E, F and G contain the aluminum polyoxo chlorocaprylate.

TABLE 1

| SAMPLE | % SALT | % ETHANOL | VISCOSITY 2.5 RPM | 10 RPM |
|---|---|---|---|---|
| A | 0 | 0 | 236 | 275 |
| B | 20.1 | 0 | 16000 | 5350 |
| C | 20 | 0.12 | 8000 | 1200 |
| D | 20 | 1.0 | 15000 | 806 |
| E | 20 | 0 | 1110 | 850 |
| F | 19.9 | 0.15 | 1020 | 845 |
| G | 19.8 | 1.1 | 944 | 836 |

What is claimed is:

1. A aluminum salt composition comprised of a composition having an empirical formula

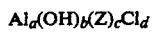

wherein Z is an anionic part of an organophilic compound; $a/(c+d)$ has the value of 0 to 3, inclusive; $c+d=3a-b$; and c is greater than 0.

2. A composition as claimed in claim 1 wherein Z is

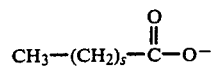

wherein s has the value of at least 1.

3. A composition as claimed in claim 2 wherein Z is

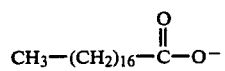

4. A aluminum-zirconium salt composition comprised of a composition having an empirical formula

wherein Z is an anionic part of an organophilic compound; k/m is greater than 0; $3k+4m=n+p+q$; and p is greater than 0.

5. A composition as claimed in claim 4 wherein k/m has the value of 2 to 10, inclusive.

6. A composition as claimed in claim 4 wherein Z is

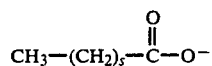

wherein s has the value of at least 1.

7. A composition as claimed in claim 5 wherein Z is

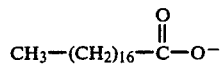

8. A composition as claimed in claim 4 wherein the aluminum-zirconium salt is further blended with an amino acid.

9. A method of inhibiting perspiration by applying to skin a composition comprising the novel aluminum salt as claimed in claim 1.

10. A method of inhibiting perspiration by applying to skin a composition comprising the novel aluminum-zirconium salt as claimed in claim 5.

11. A method of changing rheological properties of a hydrophobic liquid comprising adding to the hydrophobic liquid the composition as claimed in claim 1.

12. A method of changing rheological properties of a hydrophobic liquid comprising adding to the hydrophobic liquid the composition as claimed in claim 5.

* * * * *